(12) United States Patent
Sahud et al.

(10) Patent No.: US 11,120,681 B2
(45) Date of Patent: Sep. 14, 2021

(54) METHOD AND SYSTEM FOR MONITORING HAND HYGIENE COMPLIANCE

(71) Applicant: Allegheny-Singer Research Institute, Pittsburgh, PA (US)

(72) Inventors: Andrew Sahud, Pittsburgh, PA (US); William Rout, Pittsburgh, PA (US); Keith Lejeune, Export, PA (US); Gregory Yurko, Murrysville, PA (US); David A. Smail, Greensburg, PA (US)

(73) Assignee: ALLEGHENY-SINGER RESEARCH INSTITUTE, Pittsburgh, PA (US)

( * ) Notice: Subject to any disclaimer, the term of this patent is extended or adjusted under 35 U.S.C. 154(b) by 0 days.

(21) Appl. No.: 16/274,568

(22) Filed: Feb. 13, 2019

(65) Prior Publication Data

US 2019/0251825 A1 Aug. 15, 2019

Related U.S. Application Data

(60) Provisional application No. 62/629,986, filed on Feb. 13, 2018.

(51) Int. Cl.
| | | |
|---|---|---|
| *A47K 5/12* | (2006.01) | |
| *G08B 21/24* | (2006.01) | |
| *G06M 1/27* | (2006.01) | |
| *G16H 40/20* | (2018.01) | |
| *G07C 9/28* | (2020.01) | |

(52) U.S. Cl.
CPC ............ *G08B 21/245* (2013.01); *G06M 1/27* (2013.01); *A47K 5/12* (2013.01); *G07C 9/28* (2020.01); *G16H 40/20* (2018.01)

(58) Field of Classification Search
CPC .................................................. G08B 21/245
USPC ......................................................... 340/573.1
See application file for complete search history.

(56) References Cited

U.S. PATENT DOCUMENTS

| | | | | |
|---|---|---|---|---|
| 6,325,066 | B1* | 12/2001 | Hughes ..................... | A61F 5/48 128/885 |
| 2005/0266808 | A1* | 12/2005 | Reunamaki ............ | H04B 1/005 455/101 |
| 2010/0117836 | A1* | 5/2010 | Seyed Momen ......... | G01S 1/70 340/573.1 |

(Continued)

*Primary Examiner* — Qutbuddin Ghulamali
(74) *Attorney, Agent, or Firm* — Troutman Pepper Hamilton Sanders LLP

(57) ABSTRACT

A system for monitoring hygiene compliance includes multiple location tags, each configured to broadcast a unique identification number, and at least one event tag including a unique event identification tag and configured to detect an occurrence of a compliance event. The system further includes a mobile device being carried by a person that is configured to: receive the broadcast unique identification numbers from the location tags; determine a location based upon the received identification numbers; analyze the determined location against a location index to determine a compliance requirement; determine whether the person should complete a compliance event; if the person has completed a compliance event, receive the broadcast unique event identification tag and record the occurrence of the compliance event; if the person has not completed a compliance event, record a missed compliance event; and determine compliance information based upon the recorded compliance events and the recorded missed compliance events.

18 Claims, 8 Drawing Sheets

(56) References Cited

U.S. PATENT DOCUMENTS

2017/0229003 A1* 8/2017 Borke .................... G16H 40/20

* cited by examiner

METHOD AND SYSTEM FOR MONITORING HAND HYGIENE COMPLIANCE

CROSS REFERENCE TO RELATED APPLICATIONS

This application claims priority to U.S. Provisional Application No. 62/629,986, filed on Feb. 13, 2018, entitled "Method and System for Monitoring Hand Hygiene Compliance," the entirety of which is incorporated herein by reference.

TECHNICAL FIELD

This present disclosure is related to monitoring hand hygiene compliance. More specifically, the present disclosure is related to monitoring hand hygiene compliance using triggers to record zone entrance and dispensing/hygiene events.

BACKGROUND

Hospital infections and related complications are a tremendous burden to the patient, the physician, and the healthcare system. Many initiatives have been implemented to combat these problems and yet, ultimately, hand hygiene is still the single most effective means of stopping the spread of infection.

A tool for tracking hygiene such as hand washing which is simple, easy to adopt, inconspicuous, and which can provide improved real time, or near-real time, feedback can facilitate improved hygiene, not only in hospital environments but in any environment where cleanliness, health, and hand hygiene are of importance.

SUMMARY

In an embodiment, a system for monitoring hygiene compliance is provided. The system can include a plurality of location tags, wherein each of the plurality of location tags comprises a unique identification number and is configured to broadcast its associated unique identification number; at least one event tag comprising a unique event identification tag, the at least one event tag configured to detect an occurrence of a compliance event and broadcast the unique event identification tag in response to detecting the occurrence of the compliance event; and a mobile computing device being carried by a person. The mobile computing device can be configured to: receive at least one of the broadcast unique identification numbers from the plurality of location tags; determine a location of the person based upon the received at least one of the broadcast unique identification numbers; analyze the determined location against a locally stored location index to determine a compliance requirement for the person; determine whether the person should complete a compliance event based upon the determined compliance requirement; if the person has completed a compliance event, receive the broadcast unique event identification tag and record the occurrence of the compliance event; if the person has not completed a compliance event, record a missed compliance event; and determine compliance information for the person based upon the recorded compliance events and the recorded missed compliance events.

In another embodiment, a computing device is provided. The computing device can include a processing device and a computer readable medium operably connected to the processing device and configured to store one or more instructions that, upon execution, cause the processing device to perform an algorithm. The algorithm can be configured to: receive, upon initialization of the computing device, a locally stored location index, the locally stored locating index comprising a master list of tag identification numbers and location information associated with the tag identification numbers; determine a location of a person within a specific zone, wherein the person is associated with the computing device; analyze the determined location against a locally stored location index to determine a compliance requirement for the person; determine whether the person should complete a compliance event based upon the determined compliance requirement, wherein determining whether the person should complete a compliance event comprises determining whether the person has completed a local or recent wash event and determining whether the person is in a clean hand state or a dirty hand state; if the person has completed a compliance event, record an occurrence of the compliance event and the determined location of the person during the compliance event; if the person has not completed a compliance event, record a missed compliance event; determine compliance information for the person based upon the recorded compliance events and the recorded missed compliance events; and transmit the compliance information to a database stored on a remote computing device when operably connected to the remote computing device.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings.

DETAILED DESCRIPTION

Figure 1:
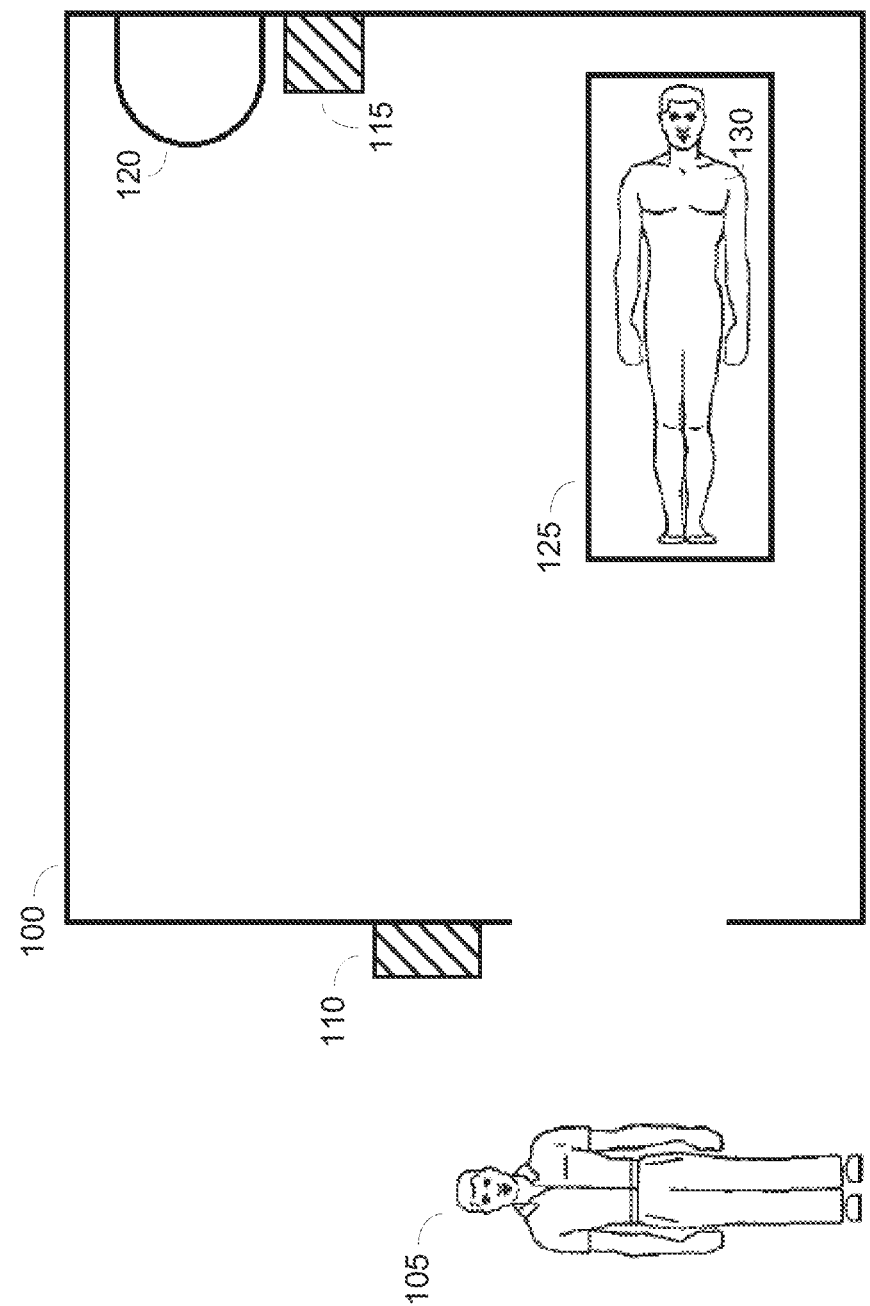
FIG. 1 illustrates a sample schematic diagram of a patient's room in a healthcare facility.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

The present disclosure is directed to a zone-based hygiene monitoring system. The system includes multiple tags located at geographically distinct areas, the tags configured to broadcast a radio frequency (RF) signal (e.g., a Bluetooth signal) defining a specific zone. A person that travels throughout the various zones, e.g., a nurse or other similar healthcare worker, can carry a mobile device such as a smartphone that includes a hygiene compliance application. The application can be configured to utilize an RF receiver or transceiver integrated into the mobile device (e.g., a Bluetooth transceiver) to monitor the person's movement throughout the zones. Additionally, the system can include event monitoring tags that are configured to detect when an event occurs. For example, an event monitoring tag can be placed onto a soap or sanitizing gel dispenser and configured to detect a dispensing event. The event monitoring tag can output an event signal to the person's mobile device. The hygiene compliance application can then assess the person's location and proximity to the dispensing event (e.g., time of the event).

In one implementation of the system as described herein, the tags can be configured to act independently, without instruction from or communicating information to a remote computing device such as a central server. Rather, information related to movement of the person throughout the zones, dispensing events, and overall hygiene compliance for the person can be tracked and monitored by the hygiene compliance application on the person's mobile device. The hygiene compliance application can further be configured to communicate directly with the remote computing device when the person's mobile device is operably connected to an external communications network (e.g., a wireless local area network in a hospital or other similar healthcare facility) and can report movement and compliance information directly to the remote computing device.

It should be noted that the following discussion of the system and associated processes as taught herein is directed to a healthcare worker such as a doctor interacting with the system within a healthcare facility such as a hospital. However, it should be noted that the ideas and techniques as taught herein are applicable to additional industries where hygiene compliance is important. For example, as shown in FIG. 7 and explained in the accompanying description below, the techniques as taught herein can be applied to the food service industry as well. However, for exemplary purposes, the following discussion of FIGS. 1-6 is directed to a healthcare environment.

FIG. 1 illustrates a portion of a healthcare facility. For example, as shown in FIG. 1, a healthcare facility such as a hospital may include various rooms or other similar areas dedicated to patient treatment. As shown in FIG. 1, a healthcare worker 105 may be approaching patient room 100. Outside of the room 100, there may be a dispenser 110 filled with and configured to dispense an amount of disinfecting or sanitizing gel. Prior to entering the room 100, the healthcare worker 105 may be required to apply an amount of the sanitizing gel to their hands. Depending upon the type of entryway into the patient's room 100, the healthcare worker 105 may be further required to wash their hands upon entering the room. For example, if the healthcare worker 105 has to actuate a handle or doorknob to enter the room 100, the healthcare facility may have a policy that requires the healthcare worker wash or otherwise sanitize their hands again prior to contacting the patient. In some examples, the healthcare worker 105 may be required to wash their hands when entering room 100 if they have not previously washed or sanitized their hands within a predetermined period of time or since the occurrence of a specific event (e.g., since their last encounter with a patient).

As shown in FIG. 1, the patient's room 100 may also include a soap dispenser 115 and a sink 120. As noted above, in certain instances the healthcare worker 105 may be required to wash their hands at the sink 120 (using, for example, soap from dispenser 115) prior to interacting with the patient 130. Once the healthcare worker 105 has satisfied the hand hygiene requirements, the healthcare worker can approach bed 125 and interact with the patient 130.

After the patient interaction, the healthcare worker 105 can again sanitize their hands. For example, the healthcare worker 105 may wash their hands using the sink 120 and soap from the dispenser 115. Additionally or alternatively, the healthcare worker 105 may sanitize their hands using sanitizing gel as dispensed from dispenser 110.

Depending upon the hygiene policy for the healthcare facility, healthcare workers such as doctors, nurses, and others who regularly interact with patients may be required to wash or otherwise sanitize their hands prior to and following each interaction with a patient. Monitoring individuals for hand hygiene and measuring compliance rates for those that interact with patients can be difficult and often requires monitoring systems that rely on complex tracking and monitoring devices and processes. Additionally or alternatively, the monitoring may be done through simple human observation programs. The system and processes as described herein, especially in regard to FIGS. 2-6 as described below, improve on existing hygiene monitoring approaches while providing accurate and real-time compliance statistics to the individuals that are subject to various hygiene policies.

Figure 2:
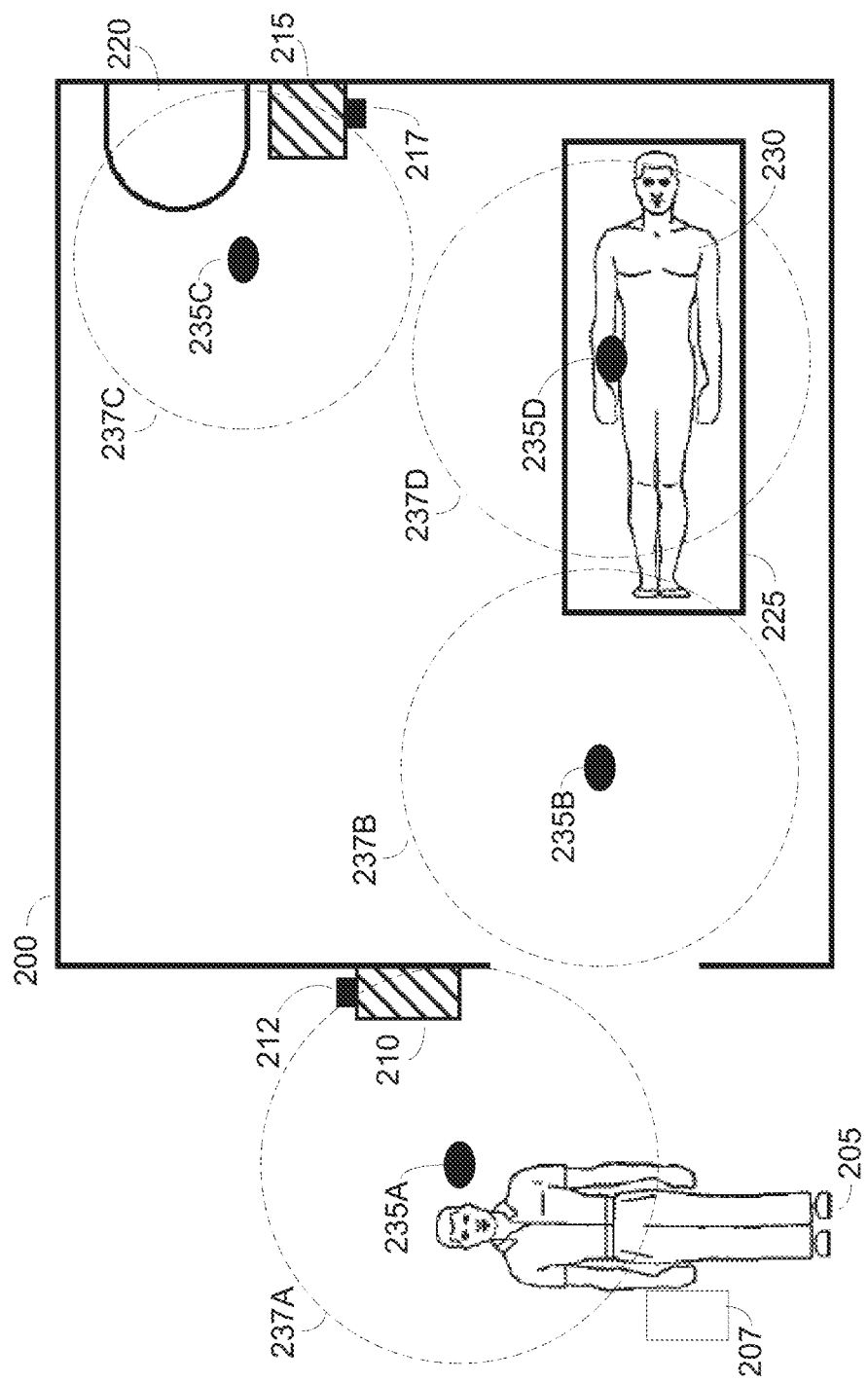
FIG. 2 illustrates a sample schematic diagram of a patient's room including various zones of focus in accordance with at least one embodiment.

FIG. 2 illustrates a portion of a healthcare facility including various system components for tracking a person throughout the facility and monitoring their hygiene compliance. Similar to FIG. 1, as shown in FIG. 2, a healthcare worker 205 may be approaching patient room 200. Outside of the room 200, there may be a dispenser 210 filled with and configured to dispense an amount of disinfecting or sanitizing gel. Prior to entering the room 200, the healthcare worker 205 may be required to apply an amount of the sanitizing gel to their hands. Depending upon the type of entryway into the patient's room 200, the healthcare worker 205 may be further required to wash their hands upon entering the room.

As shown in FIG. 2, the patient's room 200 may also include a soap dispenser 215 and a sink 220. As noted above in the discussion of FIG. 1, in certain instances the healthcare worker 205 may be required to wash their hands at the sink 220 (using, for example, soap from dispenser 215) prior to interacting with the patient 230. Once the healthcare worker 205 has satisfied the hand hygiene requirements, the healthcare worker can approach bed 225 and interact with the patient 230.

As shown in FIG. 2, the healthcare facility may include a number of additional components. In certain implementations, a set of mounted tags 235A-235D may be mounted at various locations throughout the facility. For example, each of the mounted tags 235A-235D can be configured to be a ceiling mounted tag that includes an RF emitter and a focusing antenna that emits a location signal within a defined cone or zone of focus. As shown in FIG. 2, each of tags 235A-235D has an associated zone 237A-237D. Each of zones 237A-237D may represent the extent or outer boundary of the defined zone of focus for each of the tags 235A-235D. In the example shown in FIG. 2, each of the zones 237A-237D is geographically located in a distinct location. For example, zone 237A (associated with tag 235A) may be positioned outside the door to room 200, zone 237B (associated with tag 235B) may be positioned inside the door to room 200, zone 237C (associated with tag 235C) may be positioned near soap dispenser 215 and sink 220, and zone 237D (associated with tag 235D) may be positioned over the patient's bed 225. In some examples, one or more of tags 235A-235D can include an infrared sensor or another similar optical sensor configured to determine additional information such as, for example, whether a particular bed is currently occupied.

Additionally, as shown in FIG. 2, the system may include event monitor tags 212 (integrated into dispenser 210) and 217 (integrated into dispenser 215). These event monitor tags 212 and 217 may be implemented as sensors configured to determine when a dispensing event has occurred at one of the dispensers 210 and 215. Upon detecting that a dispensing event has occurred, the event monitoring tag 212 or 217 that detected the dispensing event may send out a signal indicating the event occurred.

Figure 3B:
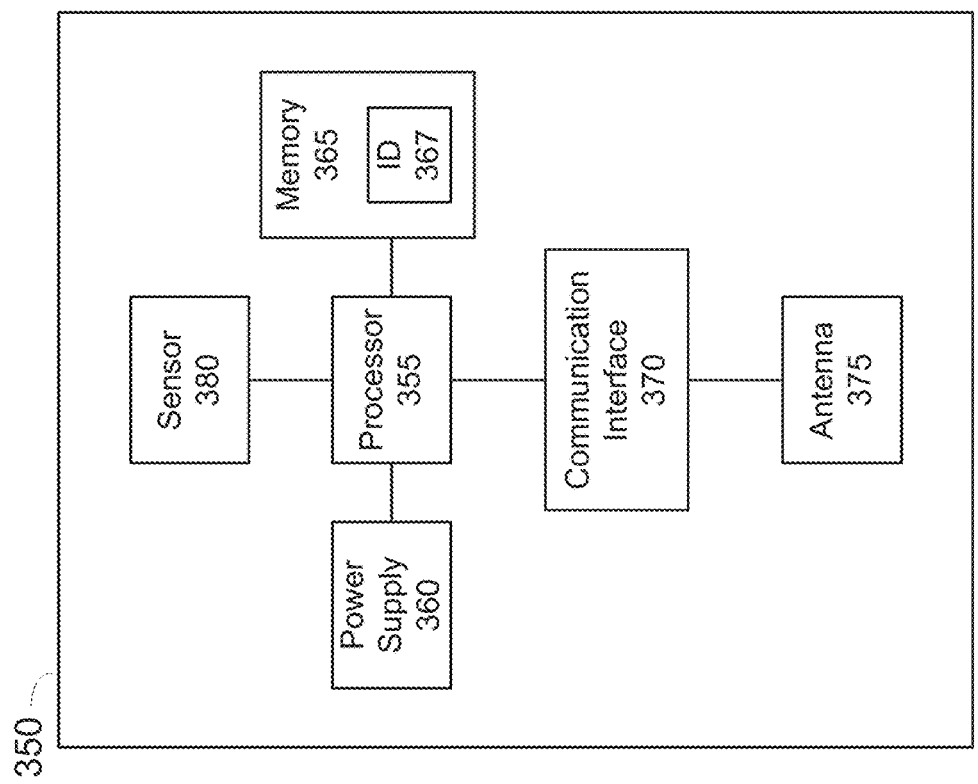
FIG. 3B illustrates a sample schematic diagram of event monitoring tag in accordance with at least one embodiment.
Figure 3A:
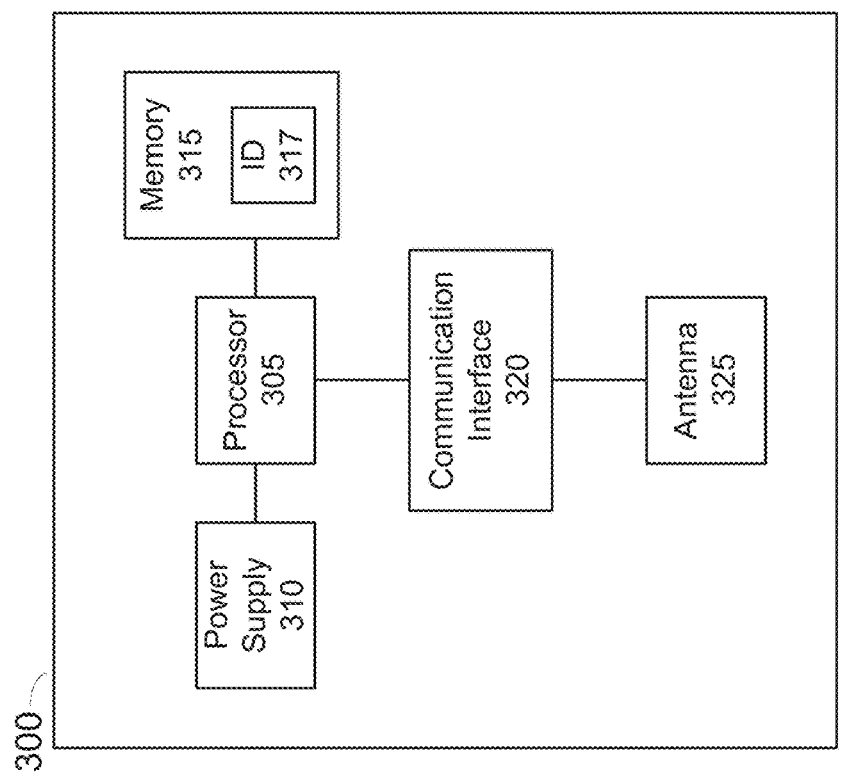
FIG. 3A illustrates a sample schematic diagram of a ceiling mounted tag in accordance with at least one embodiment.

FIGS. 3A and 3B illustrate sample circuit diagrams for a mounted tag 300 and an event monitor tag 350. As shown in FIG. 3A, a mounted tag 300, e.g., a tag configured to be mounted on a ceiling, may include a processor 305 configured to perform a series of instructions. The tag 300 may also include a power supply 310 such as a replaceable or rechargeable battery. In some implementations, the tag 300 may be hard wired into a main electrical supply to receive continuous power, and may include an alternative power supply such as a battery for backup if the main power supply fails. The tag 300 may also include a memory 315 operably connected to the processor 305. The memory 315 may include various instructions for causing the processor 305 to perform various functions. The memory 315 may also include a unique identification (ID) number 317. This unique ID number 317 may be assigned to the tag 300 when installed and may be used to identify the tag. The processor 305 may also be operably connected to a communication interface 320. For example, if the tag 300 is configured to function as a Bluetooth beacon, the communication interface 320 may be a Bluetooth transmitter or transceiver. The communication interface 320 may be operably connected to an antenna 325. As noted above, the antenna 325 may be configured or otherwise shielded to broadcast an RF signal (e.g., a Bluetooth signal) in a specific area. For example, the antenna 325 may be configured to broadcast the RF signal in a defined cone, defining a circular zone such as zones 237A-237D as shown in FIG. 2. When in operation, the processor 305 may retrieve the ID number 317 from the memory 315 and instruct the communication interface 320 to broadcast the ID number. The communication interface 320 may receive the ID number 317 from the processor 305 and broadcast the ID number via the antenna 325.

As shown in FIG. 3B, an event monitoring tag 350, e.g., a tag configured to be integrated into a dispensing device, may include a processor 355 configured to perform a series of instructions. The tag 350 may also include a power supply 360 such as a replaceable or rechargeable battery. The tag 350 may also include a memory 365 operably connected to the processor 305. The memory 365 may include various instructions for causing the processor 355 to perform various functions. The memory 365 may also include a unique identification (ID) number 367. This unique ID number 367 may be assigned to the tag 350 when installed and may be used to identify the tag. The processor 355 may also be operably connected to a communication interface 370. For example, if the tag 350 is configured to communicate using Bluetooth signals, the communication interface 370 may be a Bluetooth transmitter or transceiver. The communication interface 370 may be operably connected to an antenna 375. The tag 350 may also include a sensor 380. The sensor 380 may be configured to detect when the dispenser into which tag 350 is integrated performs a dispensing event. For example, the sensor 380 may be integrated as a vibrational sensor configured to detect movement or vibrations associated with a dispensing event. In some implementations, the sensor 380 may be another similar electronic sensor configured to detect operation of or interaction with the dispensing device. When in operation, the processor 305 may monitor the output of the sensor 380 to determine if a dispensing event has occurred. If a dispensing event has occurred, the processor 355 may retrieve the ID number 367 from the memory 365 and instruct the communication interface 370 to broadcast the ID number. The communication interface 370 may receive the ID number 367 from the processor 355 and broadcast the ID number via the antenna 375. Additionally or alternatively, the communication interface 370 may also be configured to broadcast additional information such as a time of the dispensing event, type of dispensing event, and other related information.

Referring back to FIG. 2, in the system as shown in FIG. 2 the healthcare worker 205 may carry a mobile computing device 207. In some implementations, the mobile computing device 207 may be a smartphone, a tablet computing device, or another similar portable computing device. The mobile computing device 207 may include a display and an audible and/or tactile notification system for providing information to the healthcare worker 205. The mobile device 207 may also include an RF signal receiver for receiving information transmitted by the various tags throughout the system (e.g., mounted tags 235A-235D and event monitoring tags 212 and 217). For example, if the tags are configured to transmit Bluetooth signals, the mobile computing device 207 may include a Bluetooth receiver or transceiver for receiving the Bluetooth signals.

The mobile device 207 may also include a hygiene compliance application installed therein. The hygiene compliance application may be configured to collect data related to hygiene compliance from the RF signal receiver. The hygiene compliance application may also include one or more algorithms for determining various information. For example, the hygiene compliance application may include an algorithm for determining a location of the mobile computing device 207. The hygiene compliance application may determine whether the mobile computing device 207 is within a specific zone based upon signal strength of the received RF signal. Additionally, the hygiene compliance application may determine whether the mobile computing device 207 is between zones by averaging signal strengths from multiple received signals (e.g., from multiple mounted tags).

The hygiene compliance application may also be configured to determine the status of the mobile computing device 207 within a number of defined states. For example, the hygiene compliance application may determine whether the mobile computing device 207 (and, by association, the person carrying the mobile computing device) is in a compliant or a non-compliant state. For example, if the hygiene compliance application determines the mobile computing device 207 is in a non-compliant state, the hygiene compliance application may trigger the display to provide, for example, a visual notification as well as to trigger an audible/tactile notification system to notify the person carrying the mobile computing device 207 of the current state. This notification can provide an opportunity for the person carrying the mobile device to correct the state within a set amount of time. The hygiene compliance application may also determine various compliance information such as compliance score based upon an analysis of the frequency of compliance events relative to the number of opportunities to be compliant. Additional information related to the operation of the hygiene compliance application is provided in the discussion of FIG. 5 below.

Additionally, as shown in FIG. 2, each of the zones 237A-237D may be spaced apart. However, this is shown by way of example only. In some implementations, a set of zones can be configured such that there is some amount of overlap between adjacent zones. By measuring the intensity of each received signal, a device such as mobile computing device 207 can determine which zone a person is standing in, as well as track the person's movement from one zone to another.

Figure 4:
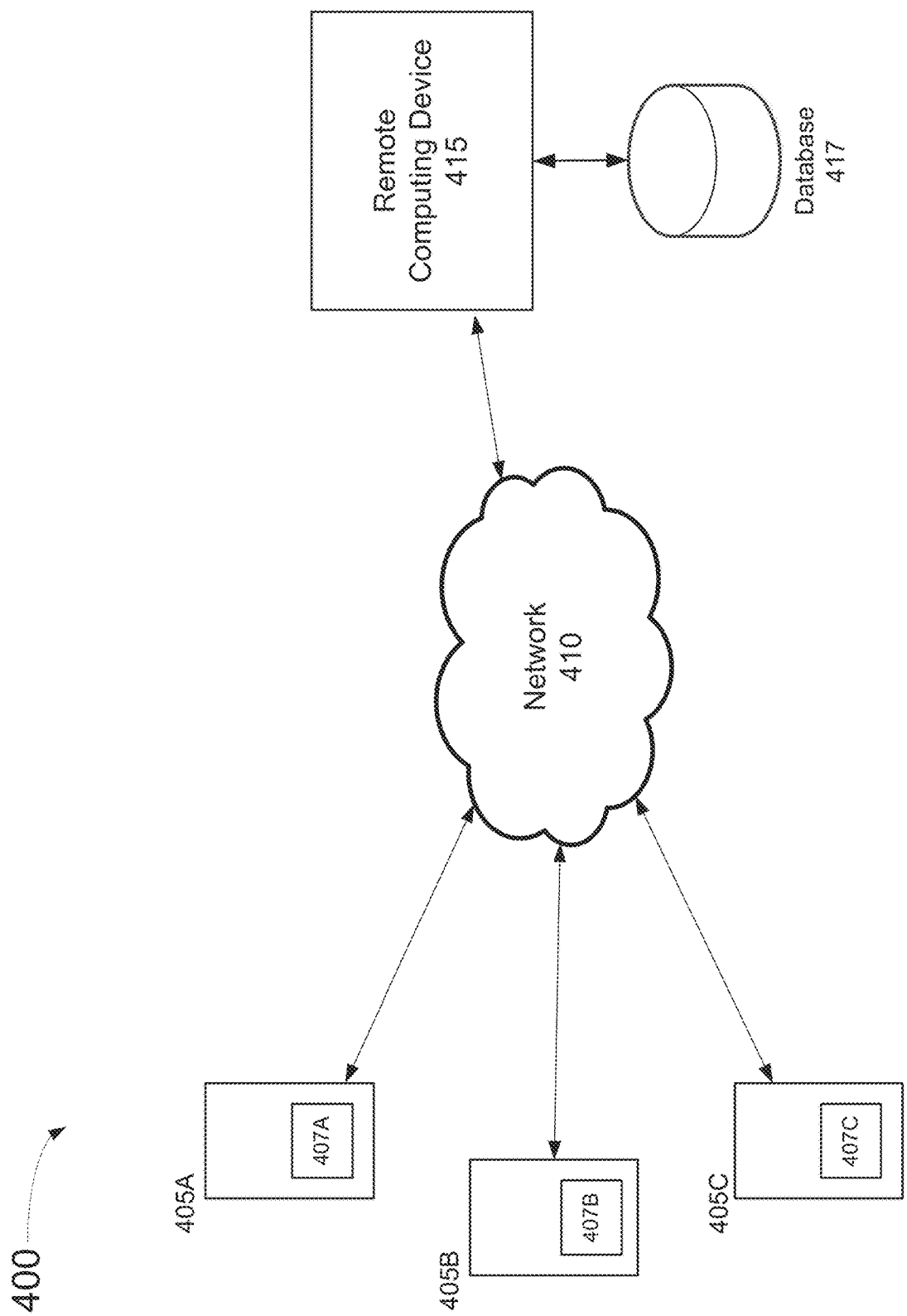
FIG. 4 illustrates a sample communication system diagram in accordance with at least one embodiment.

The hygiene compliance application as described above may also be configured to interface with a remote database operated by, for example, a remote computing device such as a remote server. The hygiene compliance application may be configured to push recorded compliance data and information to the database when, for example, the hygiene compliance application can securely connect to the database. As shown in FIG. 4, a system 400 may include multiple mobile computing devices 405A, 405B, and 405C. Each of the mobile computing devices 405A, 405B, and 405C may include an instance of the hygiene compliance application 407A, 407B, and 407C respectively. Each of the mobile computing devices 405A, 405B, and 405C may be configured to operably connect, when possible, to network 410. For example, network 410 may be a secure wireless network hosted by a healthcare facility such as a hospital. A remote computing device 415 may also be operably connected to network 410. The remote computing device 415 may include, or be configured to manage, a database 417. The database 417 may be configured to store information related to the hygiene monitoring system and processes as described herein. For example, the database 417 may be configured to store a log of tag ID numbers and information related to which zone they define. The database may also be configured to store critical parameters used to define application logic within the hygiene compliance application such as what zones require a compliance event, how long does a person have to be compliant within a particular zone, and other related information. The database 417 may also be configured to track a record of compliance events based upon information received from the mobile computing devices 405A-405C. The database 417, or the remote computing device 415, may also be further configured to facilitate report generation including compliance data for an individual, a population sub-group, or an entire population.

As noted above, the hygiene compliance application can be configured to monitor various states of a mobile computing device, and by extension the person carrying the mobile computing device. For example, the hygiene compliance application can determine wash status. The hygiene compliance application can determine a positive wash status if an event monitor tag signals a dispensing event simultaneously while the mobile computing device detects an associated RF signal at a level above a defined threshold (e.g., the device confirms that the user is within the appropriate zone of the event monitor tag). The hygiene compliance application may remain in the wash positive state for a defined amount of time (e.g., 5 seconds up to two minutes depending upon the circumstances). The hygiene compliance application may also remain in the wash positive status if the application determines that the mobile computing device has remained in a defined zone for an extended period of time and has not moved to another zone. The hygiene compliance application may determine a negative wash status if neither positive wash status condition occurs or if a particular zone counter for compliance expires.

The hygiene compliance application may also be configured to determine which zone the mobile computing device is currently in. For example, the hygiene compliance application may determine that a mobile computing device is within a particular zone when the signal strength from a mounted tag associated with a particular zone is above a threshold. Determining that a mobile computing device is within a zone may indicate a compliance opportunity. If the mobile computing device is in a positive wash state (as defined above), the hygiene compliance application may log this event as a good wash-in and indicates positive compliance. If the mobile computing device is in a negative wash state, the hygiene compliance application may trigger the mobile computing device to display a message indicating the current state for a defined amount of time. If the wash status changes to positive before the time elapses, the hygiene compliance application may record that as a positive compliance event. If, conversely, the mobile computing device remains in a negative compliance state, the hygiene compliance application may record this as a negative compliance event.

Figure 5:
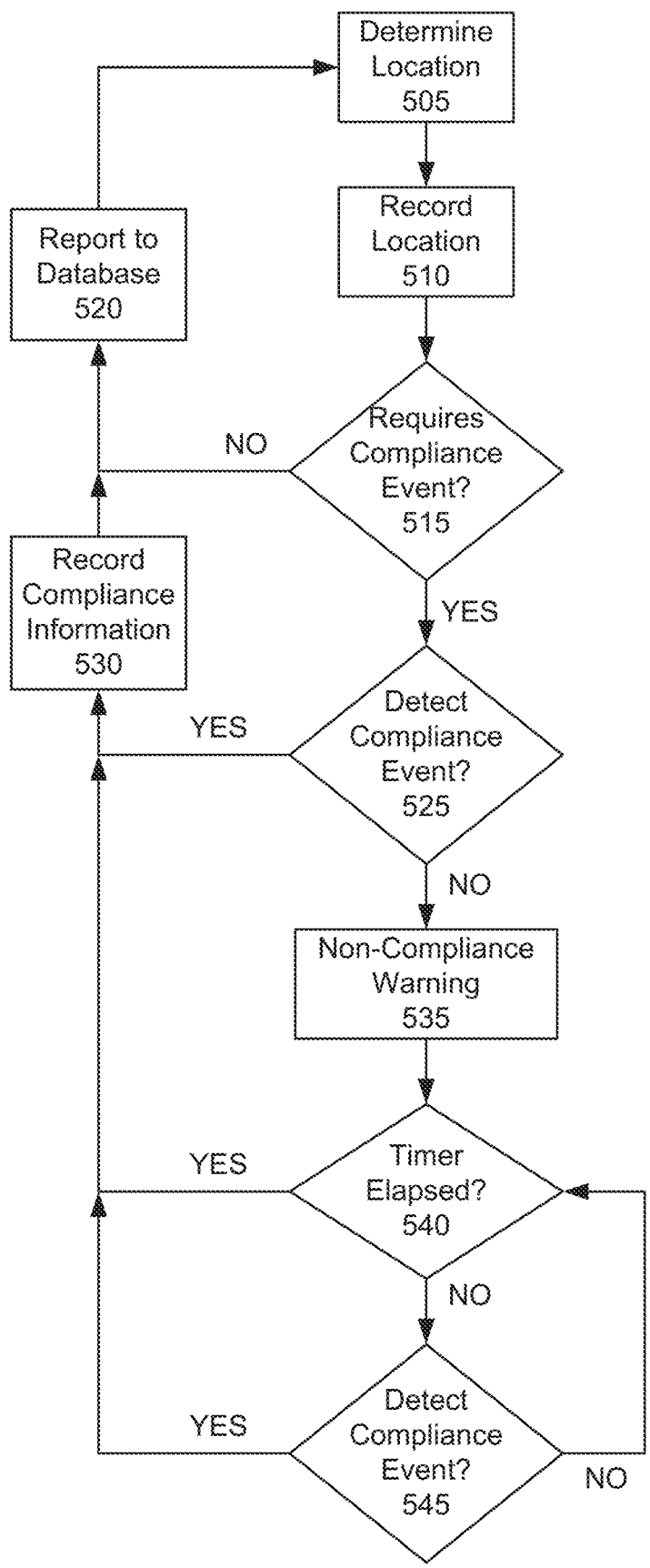
FIG. 5 illustrates a sample process flow for monitoring hand hygiene in a sample system such as that shown in FIG. 2 in accordance with at least one embodiment.

FIG. 5 illustrates a simplified process flow for the hygiene compliance application to determine compliance information for a mobile computing device. As noted above, the hygiene compliance application may be configured to determine 505 a location of the mobile computing device. The hygiene compliance application may record 510 the location information. In some implementations, the hygiene compliance application may download or otherwise receive a master list of tag information from the database. The list may include all available tag ID numbers, location information associated with the ID numbers, and other similar information. The hygiene compliance application may receive this master list whenever there are changes to tags (e.g., the system is updated to include additional tags) or at a regular time interval (e.g., every 24 hours).

The hygiene compliance application may then determine 515 if the current location of the mobile computing device requires a compliance event. If the location does not require a compliance event, the hygiene compliance application may report 520 the location information to the database (if a connection to the database is available). If the location does require a compliance event, the hygiene compliance application may determine 525 if a compliance event has occurred (e.g., is the mobile device in a positive wash-in state). If the hygiene compliance application determines 525 that a compliance event has occurred, the hygiene compliance application may record the compliance information. If the hygiene compliance application determines 525 that a compliance event has not occurred, the hygiene compliance application may display 535 a non-compliance warning and notify the user of the mobile computing device of a period of time to become compliant. The hygiene compliance application may then determine 540 whether the period of time has elapsed. If the period of time has elapsed, the hygiene compliance application may record 530 the negative compliance information. If the hygiene compliance application determines 540 that the time has not elapsed, the hygiene compliance application may continue to monitor 545 for a detected compliance event. If the hygiene compliance application does detect a compliance event before the expiration of the timer, the hygiene compliance application can record 530 the positive compliance information. If, however, the timer elapses before detecting a compliance event, the hygiene compliance application may record 530 the negative compliance information.

The hygiene compliance application may also be configured to track movement of the mobile computing device. For example, once the hygiene compliance application has detected a zone of focus, it can measure changes in average signal strength to define additional compliance opportunity. If the mobile device attains a positive wash status after a first zone compliance opportunity and moves to a location that is indicative of a new zone, the hygiene compliance application may log the event as a good wash-out and a positive compliance event. If the mobile computing device moves to a new zone and has a negative wash status, the hygiene compliance application may trigger the mobile computing device to notify the user of the potential non-compliance. If the wash status changes to positive within a given time period, the hygiene compliance application may record a positive compliance event. If the time period expires and the mobile computing device remains in a negative state, the hygiene compliance application may record the event as a negative compliance event.

Figure 6:
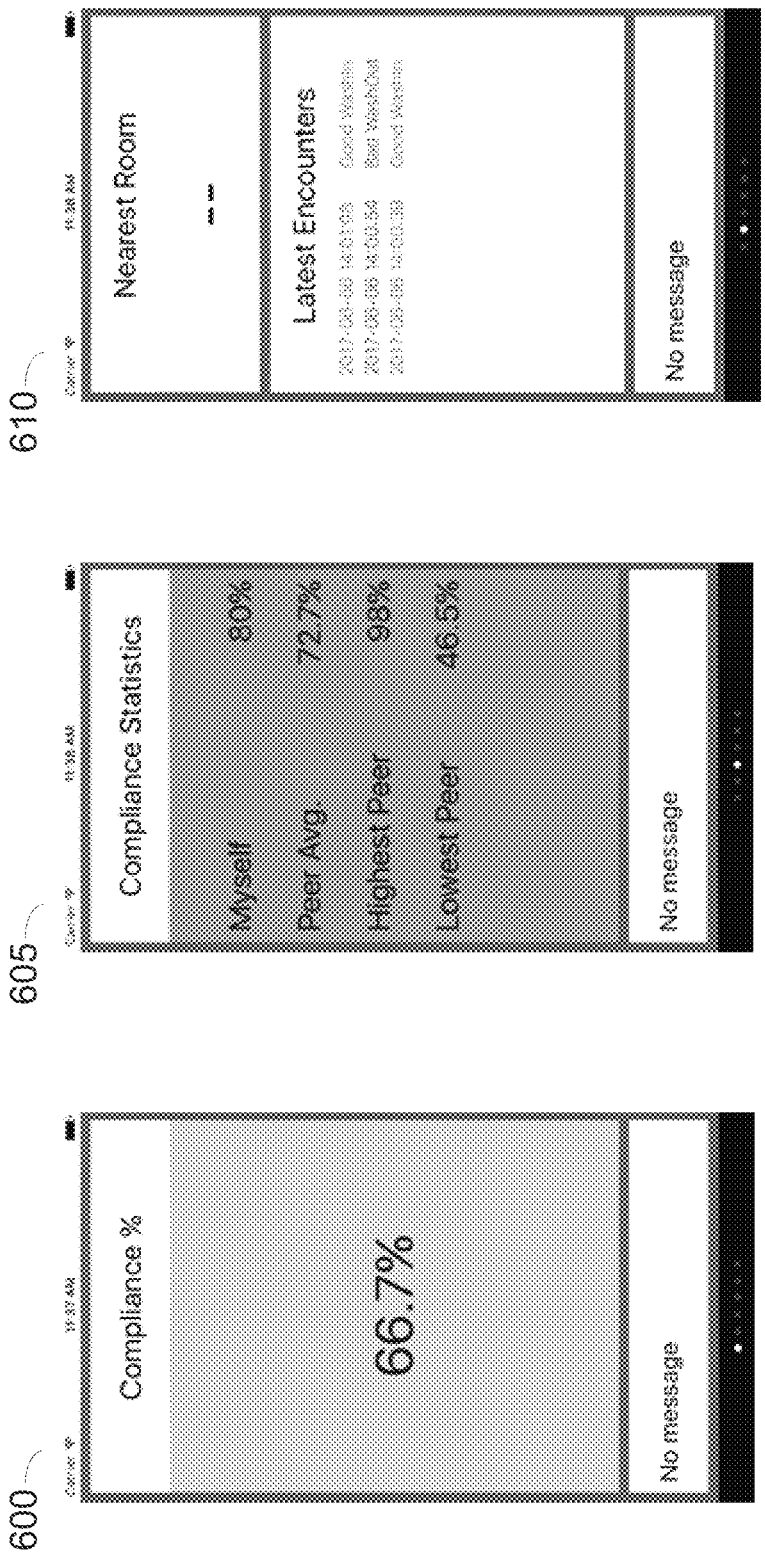
FIG. 6 illustrates various sample depictions of screenshots of an application for use with a system and method for monitoring hand hygiene in accordance with at least one embodiment.
Figure 7:
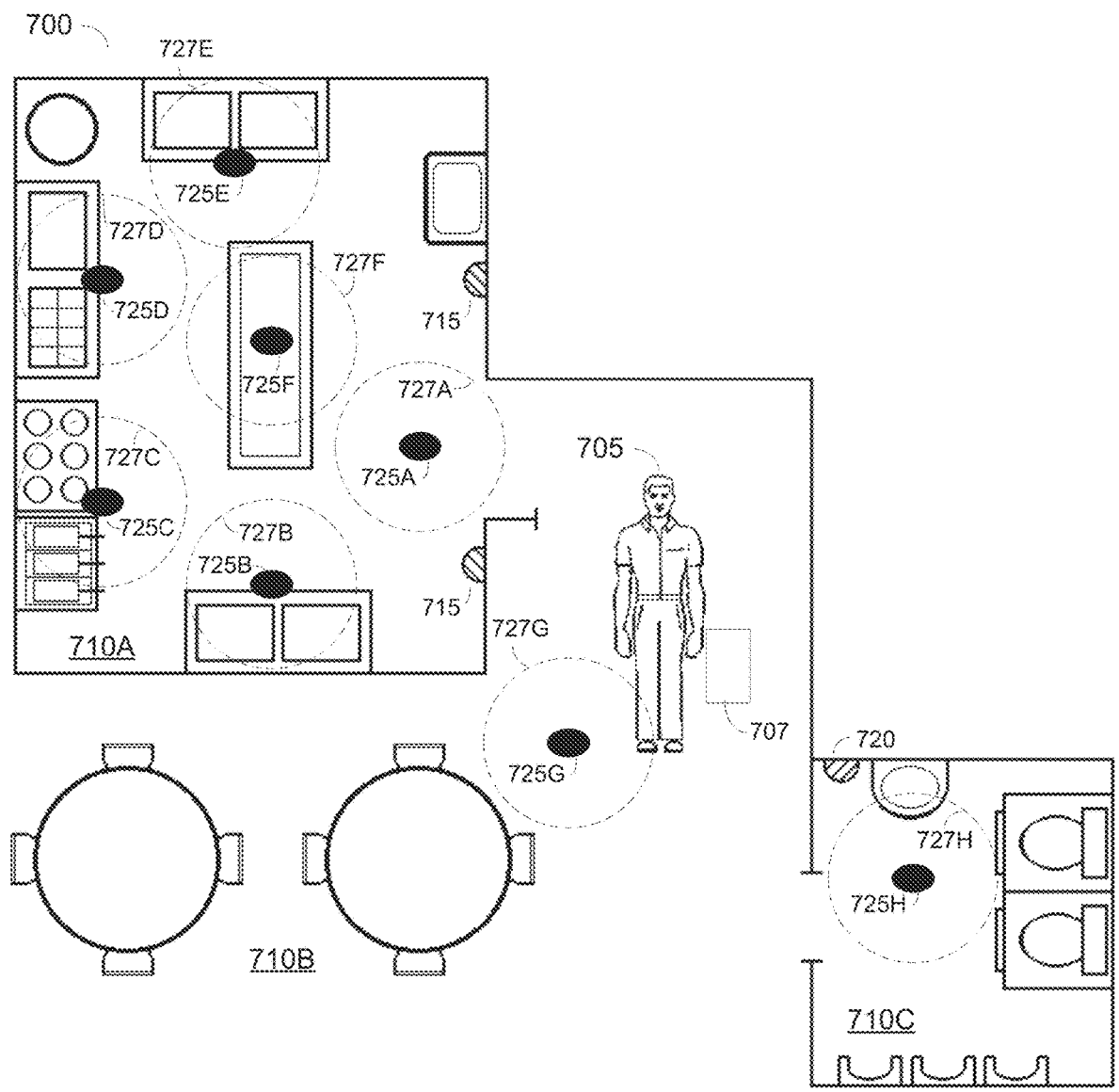
FIG. 7 illustrates an alternative sample schematic of an alternate location for implementation of the system and method for monitoring hand hygiene in accordance with at least one embodiment.

FIG. 6 illustrates various screenshots of the hygiene compliance application running on, for example, a smartphone. For example, as shown in screenshot 600, the application can be configured to display an overall compliance score or compliance percentage for the user of the smartphone running the hygiene compliance application. In some implementations, as noted above, the compliance score can be based upon a comparison of the number of recorded compliance events and the number of recorded missed compliance events. As shown in screenshot 600, the compliance percentage may be determine based upon the number of recorded compliance events compared to the total number of opportunities for a compliance event to have been completed.

Screenshot 605 includes a list of additional compliance statistics that may be displayed. In some implementations, the additional compliance statistics may be determined based upon information received from, for example, database 417 as described above. As shown in screenshot 605, the additional compliance statistics can include personal compliance percentage, an average compliance percentage for a peer group (e.g., a group of healthcare workers such as nurses or doctors), the highest percentage member of the peer group, and the lowest percentage member of the peer group.

Screenshot 610 includes a list of compliance events and encounters. For example, the hygiene compliance application may be configured to show all events within a time period (e.g., within the last hour) or show a partial listing of all events (e.g., whatever portion of the list fits on the smartphone screen). The user of the smartphone may have the option to scroll or otherwise access additional events or encounters as listed by the hygiene compliance application. For example, at the end of an 8-hour shift, the user of the smartphone may be able to access the hygiene compliance application and review a listing of all compliance events and encounters to determine which, if any, of the events or encounters the user missed.

Additional features such as messaging (as shown in screenshots 600, 605, and 610), geographical information such as nearest room (as shown in screenshot 610), and other related information may further be shown in the hygiene compliance application. It should be noted that the information as contained in screenshots 600, 605, and 610 is provided by way of example only, and additional or alternative information can be illustrated or displayed by the hygiene compliance application. For example, the hygiene compliance application can further include a graphical representation or map of a designated facility. By determining a location of the user and the smartphone, the hygiene compliance application can overlay information onto or update the map to reflect a current location of the user within a designated facility such as a healthcare facility. For example, if the user has received instructions to report to a specific area or patient room within a healthcare facility, the hygiene compliance application can display that message as well as provide location information.

As noted above, the systems, processes, and techniques as described herein were discussed in a healthcare environment by way of example only. However, the teachings of the present disclosure can be applied to additional industries where hygiene is important. For example, additional industries can include, but are not limited to, food processing facilities, pharmaceutical manufacturing facilities, cleanroom environments such as computer processor manufacturing facilities, childcare facilities, nursing homes, and other similar industries and environments.

One specific industry where hygiene is important, and the systems, processes, and techniques as described herein can be integrated, is restaurants and other similar food preparation facilities. FIG. 7 illustrates a sample restaurant 700 that includes various components and systems as described herein for monitoring hygiene compliance of employees such as server 705. As the server 705 moves throughout the restaurant 700, their location may be tracked and, if they are in an area that requires a hygiene compliance event, their hygiene compliance may be monitored. As shown in FIG. 7, the restaurant 700 may be divided into several main areas such as kitchen 710A, dining area 710B, and bathroom 710C. Various hygiene dispensers may be distributed throughout the restaurant 700. For example, two soap and/or sanitizing gel dispensers 715 may be placed within the kitchen 710A, and a soap dispenser 720 may be placed within the bathroom 710C. It should be noted that the dispenser locations are shown by way of example only and additional dispensers may be positioned throughout the restaurant 700. It should also be noted that the layout of and inclusion of various areas within the restaurant 700 is solely for exemplary purposes, and in actual use the location and number of the system components as described herein can vary accordingly based upon the actual restaurant the system is being integrated into.

Referring again to FIG. 7, a set of mounted tags 725A-725H can be placed throughout the restaurant 700, each of the tags having an associated zone 727A-727H respectively. Similar to the discussion of FIG. 2, each of the set of mounted tags 725A-725H can be related to a specific geographic area of the restaurant 700. For example, tags 725A-725F can be in the kitchen 710A, tag 725G may be in the dining area 710B, and tag 725H may be placed in the restroom 710C. Within the kitchen 710A, each of the tags 725A-725F can be located in a specific area of the kitchen. For example, tag 725A (and associated zone 727A) may be positioned near the entrance to the kitchen, tag 725B (and associated zone 727B) may be positioned near a meat preparation station, tag 725C (and associated zone 727C) may be positioned near one or more cooking appliances, tag 725D (and associated zone 727D) may be positioned near a salad preparation station, tag 725E (and associated zone 727E) may be positioned near a fruit and vegetable preparation station, and tag 725F (and associated zone 727F) may be positioned near an expeditor station where plated dishes are ordered and arranged for delivery to the dining area 710B.

As noted above in the discussion of FIG. 2, each of the tags 725A-725H may be configured to continually broadcast a unique ID number within its associated zone. Additionally, similar to the discussion of FIG. 2, each of the dispensers 715 and 720 may include an event monitor tag integrated therein and configured to send out a signal when a compliance event occurs at the dispenser (e.g., dispensing of soap or a sanitizing gel).

The movement and hygiene compliance of the server 705, or any employee of the restaurant, may be monitored by a mobile computing device 707 carried by the server 705 (or other employee) and running a hygiene compliance application using the processes as described herein. Each of the zones 727A-727H may also have one or more hygiene compliance parameters that define whether a hygiene event is required for the server 705. For example, when in the dining room 710B (e.g., within zone 727G), the server 705 may not be required to perform a compliance event in response to the server moving to another zone. Conversely, when in the bathroom 710C (e.g., within zone 727H), the server may be required to perform a hygiene compliance event regardless of the time spent within the zone.

In the kitchen 710A, hygiene rules may be determined by what specific zone a person is in and for how long they are in the zone. For example, if server 705 passes through zone 727B (associated with the meat preparation station) on their way to another area, they may not be required to perform a hygiene event. However, if the server 705 remains in the meat preparation station zone 727B for an extended period of time (e.g., more than 30 seconds), this may register in the hygiene compliance application as a situation where a compliance event is required. The hygiene compliance application can display or otherwise output (e.g., via a vibration or other tactile feedback) that the server 705 needs to perform a hygiene event.

It should be noted that the examples as described above are intended for explanatory purposed only. The systems, processes, and techniques as described herein can be applied to additional functionality than monitoring hygiene compliance. For example, tracking a person's movement throughout a set of zones can be used for mapping purposes as well. An application may include a set of maps for a specific area or structure such as an office building. By determining the person's current location (e.g., what zone are they currently in), the application can display updated locational information to the person. Additionally, if the person has an appointment or meeting, the application can access that information, determine location information for the appointment or meeting, and determine a set of directions for guiding the person from their current location to their destination. A similar process can be used for targeting advertising to a person in a store or other similar retailer. By determining what zone a person is in, an application can determine what merchandise the person is near and can provide advertisements targeted to that merchandise.

Figure 8:
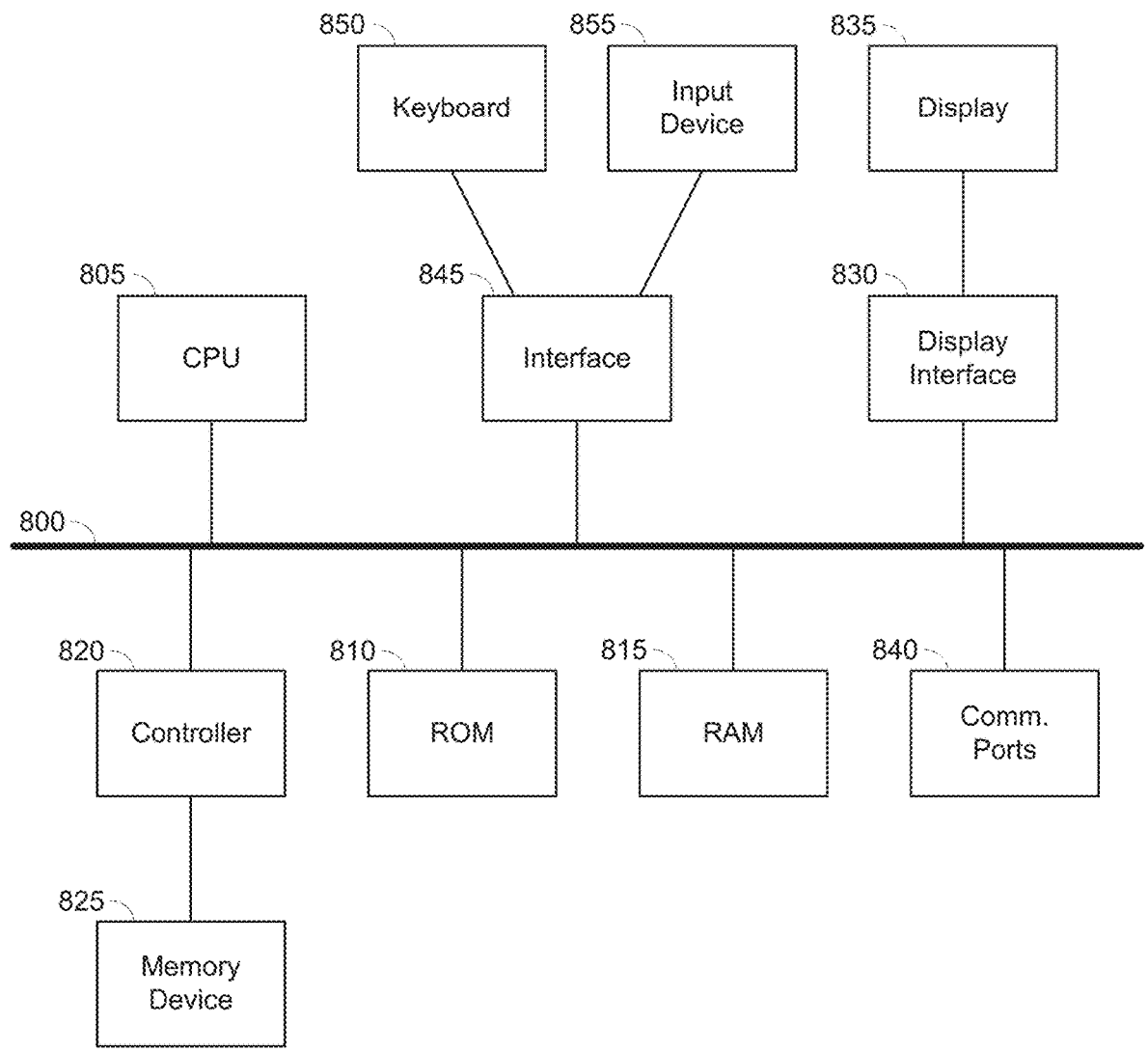
FIG. 8 illustrates various embodiments of a computing device for implementing the various methods and processes described herein.

FIG. 8 depicts a block diagram of exemplary internal hardware that may be used to contain or implement the various computer processes and systems as discussed above. A bus 800 serves as the main information highway interconnecting the other illustrated components of the hardware. CPU 805 is the central processing unit of the system, performing calculations and logic operations required to execute a program. CPU 805, alone or in conjunction with one or more of the other elements disclosed in FIG. 8, is an exemplary processing device, computing device or processor as such terms are used within this disclosure. Read only memory (ROM) 810 and random access memory (RAM) 815 constitute exemplary memory devices.

A controller 820 interfaces with one or more optional memory devices 825 to the system bus 800. These memory devices 825 may include, for example, an external or internal DVD drive, a CD ROM drive, a hard drive, flash memory, a USB drive or the like. As indicated previously, these various drives and controllers are optional devices. Additionally, the memory devices 825 may be configured to include individual files for storing any software modules or instructions, auxiliary data, common files for storing groups of results or auxiliary, or one or more databases for storing the result information, auxiliary data, and related information as discussed above. For example, the memory devices 825 may be configured to store data entry records, data entry information or any other information used by hygiene monitoring systems as described herein.

Program instructions, software or interactive modules for performing any of the functional steps associated with monitoring hygiene compliance as described above may be stored in the ROM 810 and/or the RAM 815. Optionally, the program instructions may be stored on a tangible computer-readable medium such as a compact disk, a digital disk, flash memory, a memory card, a USB drive, an optical disc storage medium, such as a Blu-Ray™ disc, and/or other recording medium.

An optional display interface 830 may permit information from the bus 800 to be displayed on the display 835 in audio, visual, graphic or alphanumeric format. Communication with external devices may occur using various communication ports 840. An exemplary communication port 840 may be operably connected via a wired and/or wireless connection to a communications network, such as the Internet or a local area network.

The hardware may also include an interface 845 which allows for receipt of data from input devices such as a keyboard 850 or other input device 855 such as a mouse, a joystick, a touch screen, a remote control, a pointing device, a video input device and/or an audio input device.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $1/10$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for monitoring hygiene compliance, the system comprising:
   a plurality of location tags, wherein each of the plurality of location tags comprises a unique identification number and is configured to broadcast its associated unique identification number;
   at least one event tag comprising a unique event identification tag, the at least one event tag configured to:
      detect an occurrence of a compliance event, and
      broadcast the unique event identification tag in response to detecting the occurrence of the compliance event; and
   a mobile computing device being carried by a person, the mobile computing device comprising:
      a processor; and
      a non-transitory computer readable medium operably connected to the processor and configured to store one or more instructions that, upon execution, cause the mobile computing device to perform an algorithm in real time, the algorithm containing instructions which cause the mobile computing device to:
         receive at least one of the broadcast unique identification number from the plurality of location tags,
         determine a location of the person based upon the received at least one of the broadcast unique identification numbers,
         analyze the determined location against a locally stored location index to determine a compliance requirement for the person,
         determine whether the person should complete a compliance event based upon the determined compliance requirement,
         if the person has completed a compliance event, receive the broadcast unique event identification tag and record the occurrence of the compliance event,
         if the person has not completed a compliance event, record a missed compliance event, and
         determine compliance information for the person based upon the recorded compliance events and the recorded missed compliance events,
         wherein the determined location of the person is locally stored on the mobile computing device.

2. The system of claim 1, wherein the plurality of location tags comprises a plurality of ceiling mounted beacons, wherein each of the ceiling mounted beacons is configured to broadcast its associated unique identification number as a wireless transmission signal.

3. The system of claim 2, wherein each of the ceiling mounted beacons comprises a Bluetooth beacon configured to broadcast its associated unique identification number as a Bluetooth signal.

4. The system of claim 2, wherein each of the ceiling mounted beacons comprises a directional antenna configured to emit the RF signal in a defined zone.

5. The system of claim 2, wherein each of the ceiling mounted beacons is configured to continually broadcast its associated unique identification number.

6. The system of claim 1, wherein the at least one event tag is integrated into a dispensing device.

7. The system of claim 6, wherein the at least one event tag comprises a electronic sensor configured to determine a dispensing event by the dispensing device.

8. The system of claim 7, wherein the electronic sensor comprises a vibrational sensor.

9. The system of claim 7, wherein the dispensing device comprises at least one of a soap dispenser and a sanitizing gel dispenser.

10. The system of claim 1, wherein the mobile computing device is further configured to display the compliance information.

11. The system of claim 10, wherein the compliance information comprises at least a compliance score determined based upon a comparison of the recorded compliance events and the recorded missed compliance events.

12. The system of claim 1, wherein the mobile computing device is further configured to display a compliance reminder notification to the person to attain a higher level of compliance.

13. The system of claim 1, wherein the mobile computing device is further configured to display compliance information related to at least one of an individual, a population sub-group, and a population.

14. The system of claim 1, wherein the mobile computing device is further configured to receive, from a database at a remote computing device, an updated copy of the locally stored location index, the locally stored locating index comprising a master list of tag identification numbers and location information associated with the tag identification numbers.

15. The system of claim 14, wherein the mobile computing device is further configured to transmit the compliance information to the database when operably connected to the remote computing device.

16. The system of claim 1, wherein the mobile computing device is further configured to:
   access sensor location information from a database of sensor locations;
   average received signal strength from a plurality of in-range location tags; and
   determine a location of the mobile computing device based upon the average received signal strength.

17. A computing device comprising:
   a mobile processing device; and
   a non-transitory computer readable medium operably connected to the mobile processing device and configured to store one or more instructions that, upon execution, cause the mobile processing device to perform an algorithm in real time, the algorithm configured to:
      receive, upon initialization of the computing device, a locally stored location index, the locally stored locating index comprising a master list of tag identification numbers and location information associated with the tag identification numbers,
      determine a location of a person within a specific zone, wherein the person is associated with the mobile processing device, and wherein the location of the person is stored locally on the mobile processing device, analyze the determined location against the locally stored location index to determine a compliance requirement for the person, determine in real time whether the person should complete a compliance event based upon the determined compliance requirement, wherein determining whether the person should complete a compliance event comprises:

determining whether the person has completed a local or recent wash event, and determining whether the person is in a clean hand state or a dirty hand state, if the person has completed a compliance event, record an occurrence of the compliance event and the determined location of the person during the compliance event, if the person has not completed a compliance event, record a missed compliance event, determine compliance information for the person based upon the recorded compliance events and the recorded missed compliance events, and transmit the compliance information to a database stored on a remote computing device when operably connected to the remote computing device.

18. The computing device of claim 17, wherein the algorithm is configured to:

access sensor location information from a database of sensor locations;

average received signal strength from a plurality of in-range location tags; and determine a location of the computing device based upon the average received signal strength.

* * * * *